United States Patent [19]

Rolls

[11] 4,088,537

[45] May 9, 1978

[54] $\Delta^1$ DEHYDROGENATION OF CORTICOIDS WITHOUT SIDE CHAIN DEGRADATION BY SEPTOMYXA

[75] Inventor: James P. Rolls, Kalamazoo, Mich.

[73] Assignee: The Upjohn Company, Kalamazoo, Mich.

[21] Appl. No.: 698,060

[22] Filed: Jun. 21, 1976

[51] Int. Cl.² ............................................. C07B 29/02
[52] U.S. Cl. .................................................. 195/51 E
[58] Field of Search ..................................... 195/51 E

[56] References Cited

U.S. PATENT DOCUMENTS

| 2,902,411 | 9/1959 | Murray et al. | 195/51 E |
| 3,770,586 | 11/1973 | Kominek | 195/51 E |

Primary Examiner—Alvin E. Tanenholtz
Attorney, Agent, or Firm—Bruce Stein

[57] ABSTRACT

This invention discloses an improved biotransformation process for the introduction of a double bond between carbon atoms 1 and 2 in corticoids by Septomyxa without degradation of the corticoid side chain.

14 Claims, No Drawings

$\Delta^1$ DEHYDROGENATION OF CORTICOIDS WITHOUT SIDE CHAIN DEGRADATION BY SEPTOMYXA

BACKGROUND OF THE INVENTION

The corticoids are a particular type of steroid having the basic carbon skeletal formula:

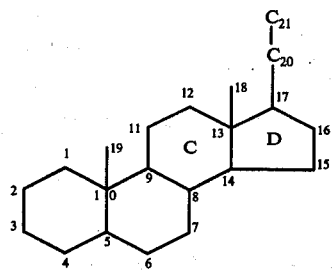

which contains 21 carbon atoms in 4 rings, A thru D.

The A-D rings of the steroid nucleus being relatively planar will have some groups, at C-11 for instance, which are positioned above ($\beta$) the plane of cyclopentenophenanthrene nucleus and are designated by —R and others which are positioned below ($\alpha$) the plane and are designated by---R.

A well-known example of the corticoids is hydrocortisone or cortisol which is represented by formula II:

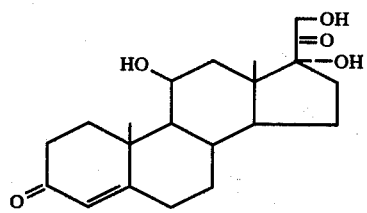

The pharmaceutical utility of the corticoids is well known to those skilled in the art. They are used for relief of inflammatory manifestations, endocrine disorders, adrenocortical insuffieiency, rheumatic disorders, dermatologic diseases, allergic states, ophthalmic diseases, respiratory diseases, hematologic disorders, neoplastic diseases, edematous states, etc.

The corticoids are administered orally, topically or parenterally in dosages and at intervals which are well known to those skilled in the art.

Many of the most potent corticoids are characterized by having a double bond between carbon atoms one and 2. This double bond between carbon atoms one and 2 is designated by $\Delta^1$. Examples of some of the more common $\Delta^1$-corticoids are prednisone (III), methylprednisolone (IV), triamcinolone (V), dexamethasone (VI), betamethasone 17$\alpha$-valerate (VII), and fluocinolone acetonide (VIII).

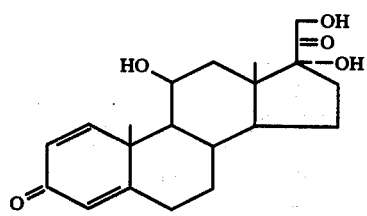

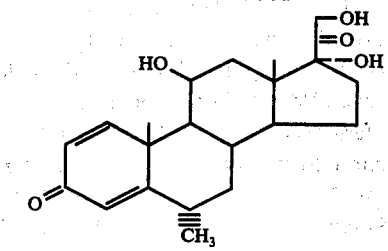

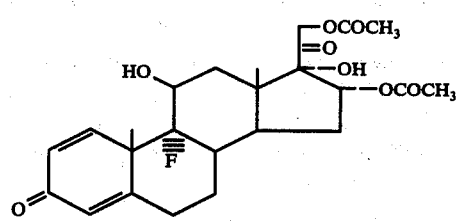

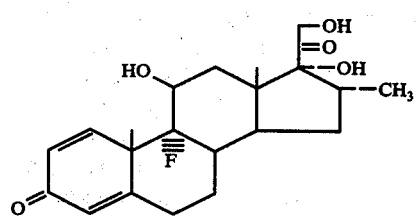

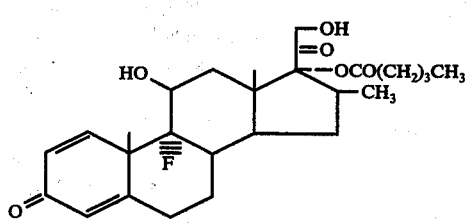

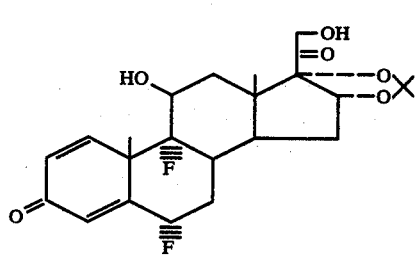

A new topical anti-inflammatory corticoid which is very potent both with and without occlusion is diflorasone diacetate (IX). See Belgium Pat. No. 796,560, British Specification 1,403,962, and German Offen. 2,308,731. The chemical formula of diflorasone diacetate is

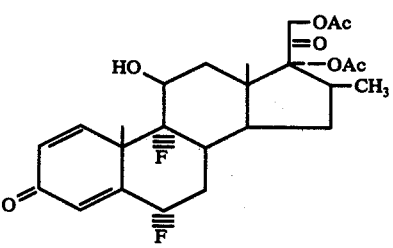

Chemical methods of introducing the $\Delta^1$ double bond into steroids are known. See J. Fried and J. A. Edwards, Reactions in Steroid Chemistry, Van Nostrand Reinhold Co. (1972), Vol. 1, Chapter 6. Some methods include the use of DDQ, chloranil and selenium dioxide, see, C. Djerassi, Steroid Reactions, Holden-Day Inc., San Francisco, 1963, page 231–4. Also used are dimethylacetamide and DMF-lithium carbonate.

Microbial fermentation methods for introducing the $\Delta^1$ double bond into steroids are also well known. See, A. Capek et al., Microbial Transformations of Steroids, Academia, Prague, 1966, page 29–30; Microbial Transformation of Steroids and Alkaloids, H. Ilzuka and A. Naito, University of Tokyo Press, Tokyo, 1967, pages 115–138 and Microbial Transformations of Steroids, W. Charney and H. L. Herzog, Academic Press, New York, 1967, page 236. In fact the microbial method of introducing the $\Delta^1$ double bond into the steroid nucleus is a cleaner reaction yielding a less complex mixture of products. Hence, the microbial method of $\Delta^1$ dehydrogenating a steroid is clearly superior to the chemical method and is the method used by the pharmaceutical industry today. For example, see U.S. Pat. Nos. 2,776,927, 2,776,928, 2,793,164, 2,822,318, 2,902,410, 2,902,411, 2,922,973, 2,951,016, 2,957,893, 2,958,631, 2,962,512, 2,968,595, 2,993,839, 3,009,937, 3,037,912, 3,037,914, 3,037,915, 3,084,103, and 3,087,864.

However, it was realized very early that $\Delta^1$ dehydrogenation of corticoids and pregnanes by most $\Delta^1$ dehydrogenating fungi resulted in destruction of the C-17 side chain. During $\Delta^1$ dehydrogenation by most fungi the C-17 side chain is degraded with the resulting $\Delta^1$ steroidal product having a C-17 alcohol, C-17 ketone or the D ring rearranged to form a 6 membered lactone. See Capek, supra, page 29; Charney, supra, pages 7–8 and U.S. Pat. No. 3,556,944. This problem is best understood by looking at a few examples:

Y. J. Abul-Hajj, J. Biol. Chem., 247, 686 (1972), and R. C. Meeks, et al., Chem. & Industry 391 (1958) reported the following reaction:

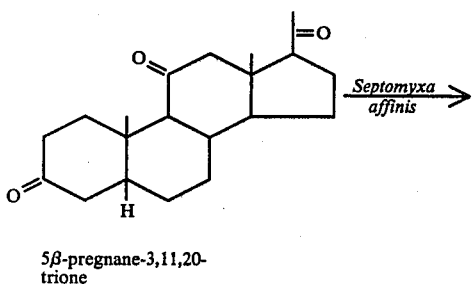

5β-pregnane-3,11,20-trione $\xrightarrow{\text{Septomyxa affinis}}$

X

5β-androst-1-ene-3,11,17-trione

XI

+

17β-hydroxy-5β-androst-1-ene 3,11-dione

XII

Also reported by Abul-Hajj, supra, was the following reaction:

5α-pregnane-3,11,20-trione $\xrightarrow{\text{S. affinis}}$

XIII

5α-androst-1-ene-3,11,17-trione

XIV

Using a different fungus, E. Vischer and A. Wettstein, Experientia 9, 371 (1953) reported progesterone $\xrightarrow{\text{Fusarium solani}}$

XV androsta-1,4-diene-3,17-dione

XVI

M. Nishikawa, et al., Pharm. Bull. (Japan) 3,322 (1955) using the same substrate (progesterone) and fungus (F. solani) identified 2 reaction products in addition to the one reported by Vischer. They are the C-17 alcohol and the 6 member D ring lactone and are set forth below:

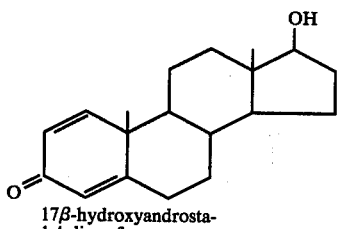

17β-hydroxyandrosta-
1,4-diene-3-one    XVII

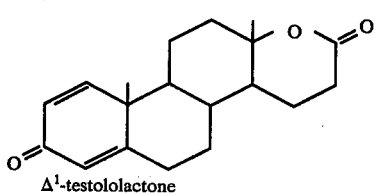

Δ¹-testololactone    XVIII

H. C. Murray and O. K. Sebek, Bact. Proc. 34 (1960), K. Singh, et al., Steroids 2, 513 (1963) and K. Singh and S. Rakhit, Biochem. Biophys. Acta 144, 139 (1967) all fermented progesterone XV with S. affinis and all obtained the formula XVI 17-keto compound and the formula XVII 17β-hydroxy compound.

J. Fried, et al., JACS 75, 5764 (1953) fermented a corticoid, Compound S, with a Δ¹ dehydrogenating fungus, *Cylindrocarpon radiciola*, and observed lactonization of the steroidal D ring:

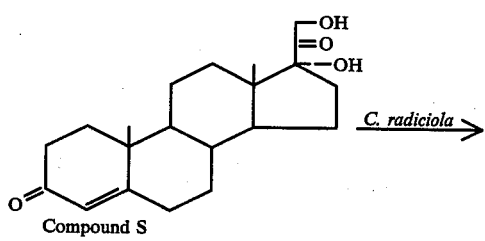

Compound S    XIX

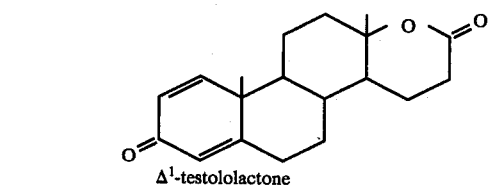

Δ¹-testololactone    XVIII

Murray, supra, K. Singh, et al., supra, and K. Singh, et al. Can. J. Microbial. 11, 351 (1965) all reported using Compound S as a substrate, but used S. affinis instead of C. radiciola and all obtained the formula XVI and XVII compounds.

Therefore, from the above examples it is readily apparent that if one starts with a pregnane or cortical steroid and subjects it to most Δ¹ dehydrogenating fungi the products obtained do include the Δ¹ double bond but in addition the side chain at the C-17 position is degraded. The C-17 position in the product is either a ketone, a hydroxyl group or the D ring is enlarged to 6 members forming a lactone. Thus, regardless of whether one starts with progesterone XV or Compound S XIX the resulting products are identical since the only difference in the starting material is the side chain at C-17.

Thus, even though most Δ¹ dehydrogenating fungi are useful in synthesizing the Δ¹ double bond to form the highly active Δ¹,⁴ A-ring they cannot always be used for this process because of the destruction of the side chain at C-17.

In fact the C-17 side chain cleavage of 20-ketopregnanes by vegetative cells of Septomyxa, and other fungi, is the subject of U.S. Pat. No. 3,556,944 (Miller). The patented process utilizes the C-17 side chain degradation to produce 17-ketoandrostanes from 20-ketopregnanes while inhibiting D-ring lactonization.

There have been reports of introduction of a Δ¹ double bond into corticoids and pregnanes by some Δ¹ dehydrogenating fungi without degradation of the C-17 side chain. See, for example, Iizuka, supra, p. 119, 122, 125, 127, 129-131 and 133.

Upon a close look at most of the papers reporting side chain retention during Δ¹ dehydrogenation by a fungus, it is noted that indeed the side chain is retained - but only transiently. In fact, the reaction sequence has been so well worked out the steps are known. The steps are first, introduction of the Δ¹ double bond, second, cleavage of the C-17 side chain to the C-17 secondary alcohol, third, oxidation to the C-17 keto compound and fourth, formation of the 6 member D-ring lactone. See, G. E. Peterson et al., J. Bacteriol. 74, 684 (1957) and M. Nishikawa Pharm. Bull. (Japan) 3,322 (1955).

M. Shiraska and M. Tsuruta, Chem. Pharm. Bull. Japan 9, 207 (1961) reported the Δ¹ dehydrogenation of Compound S and cortisone without side chain cleavage by fungi. The fungi they used were *Gliocladium roseum*, *Helminthosporium turcicum* and *Ophiobolus heterostropus*. They did not use any fungi which fall within the scope of the present invention which is limited to Septomyxa.

U.S. Pat. No. 2,951,016 (Charney) discloses Δ¹ dehydrogenation of various corticoids without side chain degradation by various molds. However, none of the organisms disclosed by Charney fall within the scope of the present invention which is limited to the genus Septomyxa. Charney disclosed that it was desirable to maintain a pH level in the reaction medium of between 6.8 and 7.2. He added, that the use of the inorganic salts for buffering the reaction mixture could be omitted. The omission of the inorganic salts causes the pH to rise from an initial value of about 6.8 to about 7.7-8.0. He stated, "this, however, will still permit the formation of the desired steroidal end products." That is not the case for the present invention. If the pH of the fermentation medium of the genus Septomyxa is not controlled so that the pH does exceed 7.0 degradation of the steroidal side chain at C-17 takes place.

G. S. Fonken et al., J. Org. Chem. 27, 1102 (1962) reported the introduction of a Δ¹ double bond into a steroid without degradation of the C-17 side chain by *S. affinis* However, the steroid was a pregnane and not a corticoid which is the subject of the present invention. It is interesting to note that the author stated, "Unfortunately incubation of 5β-pregnane-3,11,20-trione with *S. affinis* results in degradation of the side chain as well as dehydrogenation of the A ring, resulting in 5β-androst-1-ene-3,11,17-trione." To prevent side chain degradation, the 20-keto group was protected by forming a 20-ethylene ketal. Upon introduction of the Δ¹ double bond, the product was hydrolyzed to obtain the desired Δ¹ progesterone derivative.

U.S. Pat. No. 3,770,586 (Kominek) discloses a process for Δ¹ dehydrogenation of certain 4,9(11)-pregnadienes by *S. affinis* without degradation of the C-17 side chain. The steroids disclosed by Kominek are of the pregnane series and not of the corticoid type. The present invention is limited to corticoids.

S. affinis has been reported to introduce the Δ¹ double bond into a corticoid without total side chain degradation. However, the degradation of the C-17 side chain was sufficiently great that it required two steps to resynthesize the corticoid C-17 side chain. See G. B. Spero, JACS 78, 6213 (1956).

S. affinis conidia (spores) has been reported to introduce the Δ¹ double bond in corticoids without degradation of the side chain. See K. Singh et al., Steroids 2, 513 (1963). Conidia cannot be used on a commercial scale and are not included in the present invention.

U.S. Pat. No. 2,902,410 (Weintraub) discloses a process for Δ¹ dehydrogenation of 20-oxygenated steroids by Septomyxa with and without degradation of the C-17 side chain. Weintraub makes no attempt to try and prevent side chain degradation when it occurs. In fact Weintraub discloses that it is an object of the invention to provide a method for the degradation of the C-17 side chain of steroids, especially the 20-oxygenated steroids by Septomyxa. Consistent with this, is the statement in column 1, lines 50-53 that a further object of the invention was a process for the production of 17-hydroxysteroids and 17-ketosteroids.

SUMMARY OF THE INVENTION

An improved biotransformation process has been discovered whereby the fungus Septomyxa is contacted with a corticoid to introduce a Δ¹ double bond into the corticoid without loss or degradation of the side chain at C-17. This process has two essential requirements. First, the pH must be maintained at 7.0 or less during the course of the biotransformation and second, the tertiary alcohol group at C-17 be esterified.

Disclosed is an improved biotransformation process for the production of a steroid of the formula:

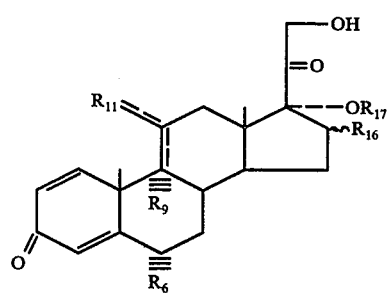   XX where $R_6$ is a hydrogen or fluorine atom or methyl group; where $R_9$ when present is a hydrogen, fluorine, chlorine, or bromine atom, or hydroxyl group; where $R_{11}$ is (H), (H,H), (H,αOH), (H,βOH) or (O); where $R_{16}$ is a hydrogen atom or methyl group; where $R_{17}$ is alkyl carboxylate of 2 thru 6 carbon atoms, aromatic carboxylate of 7 thru 12 carbon atoms, where ∼ indicates the attachment of the $R_{16}$ group in the alpha or beta configuration; and where ═ is a single or double bond; where a compound of the formula:

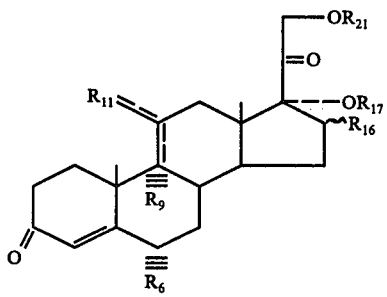   XXI where $R_6$, $R_9$, $R_{11}$, $R_{16}$, $R_{17}$, and are defined above and where $R_{21}$ is a hydrogen atom or alkyl carboxylate of 2 thru 6 carbon atoms is contacted aerobically in a fermentation medium with a fungus of the genus Septomyxa followed by extraction and purification where the improvement comprises controlling the pH of the medium so that the pH is controlled and does not exceed 7.0.

It is preferred the fungus be Septomyxa affinis. It is most preferred the fungus be S. affinis, ATCC 6737.

It is preferred the pH not exceed 6.8. It is most preferred that the pH not exceed 6.5.

It is preferred the steroid XX be diflorasone 17-acetate (6α,9α-difluoro-16β-methyl-11β,17α,21-trihydroxypregna-1,4-diene-3,20-dione 17-acetate) or 6α-fluoro-16β-methyl-17α,21-dihydroxypregna-1,4,9(11)-triene-3,20-dione 17-acetate XXIII.

It is preferred that the pH be controlled by a buffer or controlled automatically.

The formula XX steroid has an $R_{11}$ group at the C-11 position. $R_{11}$ is (H), (H,H), (H,αOH), (H,βOH), or (O). The symbol ═ represents a single or double bond. This single or double bond can be found between carbon atoms 9 and 11 in ring C and between $R_{11}$ and $C_{11}$. When $R_{11}$ is (O) there is a double bond between the $R_{11}$ group, (O), and the C-11 carbon atom. The various combinations of $R_{11}$ and the double bonds in the C ring give the following substitution of the C ring at the C-11 position:

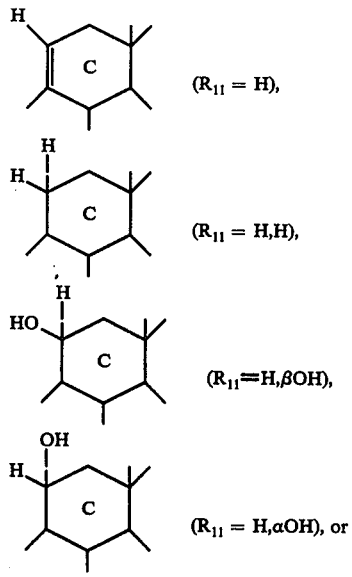

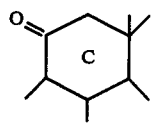

It is preferred $R_{11}$ be H. When C-11 is substituted, it is preferred that the substitution at C-11 for $R_{11}$ either be oxygen giving a 11-keto compound or a hydroxyl group in the beta position. The formula XX steroid has an $R_6$ group in the 6α position. $R_6$ is a hydrogen or fluorine atom or methyl group. The formula XX steroid has an $R_{16}$ group at the 16 position. $R_{16}$ is either a hydrogen atom or methyl group. It is preferred that $R_{16}$ be methyl. The ∼ indicates the $R_{16}$ group may be in either the α or β position. It is preferred ∼ be β. The substitution at the 9 position when present is alpha and the substituent, $R_9$, is either a hydrogen, fluorine, chlorine, or bromine atom, or a hydroxyl group. It is preferred that when the position is substituted in steroid XX that the substituent be a fluorine atom.

$R_{17}$ is alkyl carboxylate of 2 thru 6 carbon atoms or aromatic carboxylate of 7 thru 12 carbon atoms. Examples of alkyl carboxylate of 2 thru 6 carbon atoms are acetyl, propionyl, butyryl, valeryl, hexanoyl, and isomers thereof. Examples of aromatic carboxylate of 7 thru 12 carbon atoms are benzoyl, phenylacetyl, phenylpropionyl, phenylbutyryl, phenylvaleryl, phenylhexanoyl and isomers thereof.

In this invention the term contacted means fermentation with a vegetative growth, a suspension of washed or dried cells or an enzyme preparation of Septomyxa containing the $\Delta^1$ dehydrogenase. These methods are all well known to those skilled in the art. Irregardless of which method of contacting is used, the pH is controlled and does not exceed 7.0.

Microorganisms of the present invention responsible for the $\Delta^1$ dehydrogenation without C-17 side chain degradation are from the genus Septomyxa. Within the genus Septomyxa there is *S. affinis* and *S. corni*. *S. affinis* is preferred. Strains of *S. affinis* useful in the process of the present invention include, for example, *S. affinis*, ATCC 6737, *S. affinis*, ATCC 13,414, *S. affinis*, ATCC 13,425, and *S. affinis* CVS. These are available from known public sources such as the American Type Culture Collection (ATCC), Washinton, D. C. It is preferred that the strain be *S. affinis*, ATCC 6737.

As stated previously diflorasone diacetate IX is known to be a very potent topical anti-inflammatory agent both with and without occlusion. The $\Delta^1$ dehydrogenation step in the synthesis of diflorasone diacetate IX is performed by using the present invention. See Chart A.

CHART A

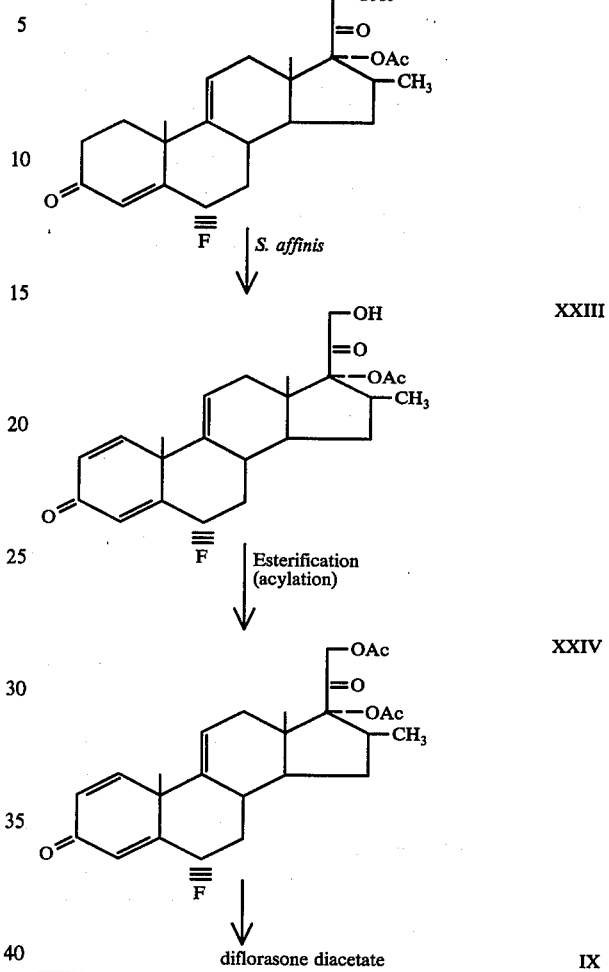

In Chart A the diacetate XXII is known in the art. See German Offen. 2,308,731. Upon contacting the formula XXII diacetate with Septomyxa according to the present invention the formula XXIII $\Delta^1$ compound is formed. See Examples 1-3. The formula XXII $\Delta^1$ compound is then acylated at the C-21 position with pyridine and acetic anhydride by methods well known to those skilled in the art. See, for example, German Offen. 2,308,731, Example 11. The product of the reaction, the formula XXIV $\Delta^1$ diacetate is then transformed to diflorasone diacetate IX by methods disclosed in German Offen. 2,308,731.

Culture of the microorganism for the purpose and practice of this invention is in or on a medium favorable to its development. Sources of nitrogen and carbon are present in the culture medium and an adequate sterile air supply is maintained during the conversion as is well known to those skilled in the art, for example, by the conventional techniques of exposing a large surface of the medium by using shake flasks or by passing air through a submerged culture.

Nitrogen in assimilable form is provided by sources normally employed in such processes which are well known in the art, such as cornsteep liquor, cottonseed meal, soybean meal, yeast extracts. Torula yeast, peptone, soluble or insoluble vegetable or animal protein, lactalbumin, casein, whey, distiller's solubles, amino acids, nitrates and ammonium compounds, such as ammonium tartrate, nitrate, sulfate and the like.

Available carbon is provided by sources normally used in bioconversions which are well known in the art such as carbohydrates, e.g., glucose, fructose, sucrose, lactose, maltose, dextrins, starches, meat extracts, peptones, amino acids, proteins, fatty acid, glycerol, sodium lactate, whey and the like. These materials are used either in a purified state or as whey concentrate, conrn-steep liquor, grain mashes, cottonseed meal, and the like, or as mixtures of the above. Many of the above sources of carbon also serve as a source of nitrogen.

The medium can also contain naturally present or added mineral constituents, such as calcium, copper, iron, potassium, phosphorus, magnesium, and the like, such as potassium phosphate, calcium chloride, ferrous sulfate, mangnesium sulfate, etc.

A temperature between about 25°to 32° C. is preferred for growth of the microorganism but higher or lower temperatures within a relatively wide range are suitable.

In carrying out the improved process of this invention, it sometimes is advantageous to pre-induce the steroid 1-dehydrogenase by adding a steroid 1-dehydrogenase inducer, such as progesterone, 3-ketobisnor-4-cholen-22-al (bisnoraldehyde), 3-ketobisnor-4-cholenic acid, androstenedione, 16α,17-epoxy-16-methylprogesterone, and the like. The selected 1-dehydrogenase inducer is added simultaneously with the substrate, during the mycelial growth period, after the growth period and before addition of the substrate or after addition of the substrate. It is, however, especially advantageous to add the 1-dehydrogenase inducer after the mycelial growth period is complete and about 2-6 hours before addition of the substrate. The quantity of inducer can vary over a wide range as illustrated by Murray et al., U.S. Pat. No. 2,902,411. In the practice of this invention, it is preferred to carry out the pre-induction at a temperature of about 28° C. and at a pH within the range of about 5.5 to 6.0 for a period of about 3–4 hours using the steroid inducer at a concentration of about 0.05 g./l. of medium. The inducer is added to the fermentation medium in a nontoxic solvent such as DMF.

The pH of the fermentation medium must not exceed 7.0. It is preferred the pH not exceed 6.8. It is most preferred that the pH not exceed 6.5. The pH may be as low as about 4 but this is rare because as Septomyxa grows the pH rises. The rises in pH is controlled by addition to the fermentation medium of any physiological buffer such as phosphate, acetate, citrate, or tartrate in sufficient amounts at sufficient concentration such that the final concentration of the buffer in the fermentation medium is from about 0.01 to about 0.2 M. The preferred buffer is phosphate and its preferred final concentration is 0.1 M. Instead of addition of a buffer to the fermentation medium the pH may be controlled by an automatic pH control system which adds small amounts of dilute (.001–0.1 N) inorganic acids such as hydrochloric, sulfuric or phosphoric to the fermentation medium to keep the pH at the desired level. The automatic pH control titrates the medium with acids such as hydrochloric, sulfuric or phosphoric. See Example 4. The pH must not exceed 7.0 from the time the substrate is added to the fermentation medium thru the time the product is extracted.

If the pH is not controlled but permitted to follow its natural course the pH of the fermentation medium will be 8.0. See H. J. Koepsell, Biotechnology and Bioengineering 4, 57 (1962).

The problem of C-17 side chain degradation of corticoids by Septomyxa when the pH is not controlled is known and set forth above. Summarizing; Murray, et al., Bact. Proc. 34 (1960), K. Singh et al., Steroids 2, 513 (1963) and K. Singh et al., Can. J. Microbiol. 11, 351 ( 1965) all reported

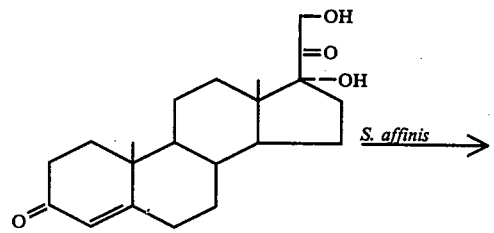

XIX

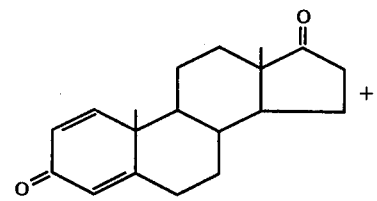

XVI

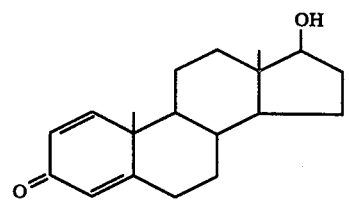

XVII

U.S. Pat. No. 2,902,410 discloses a process for Δ¹ dehydrogenation of 20-oxygenated steroids with accompanying degradation of the C-17 side chain to give 17-hydroxy and 17-keto Δ¹-steroids.

The requirement of (1) C-17 esterification and (2) control of the pH so that is does not exceed 7.0 during biotransformation are not necessary in 100% of the Δ¹ dehydrogenations in order to prevent C-17 side chain degradation of corticoids during contacting with Septomyxa. For example, 6α-fluoro-16β-methyl-17α,21-dihydroxypregna-4,9(11)-diene-3,20-dione XXVI was fermented with S. affinis under normal fermentation conditions without pH control and the product was identified as 6α-fluoro-16β-methyl-17α,21-dihydroxypregna-1,4,9(11)-triene-3,20-dione XXVII.

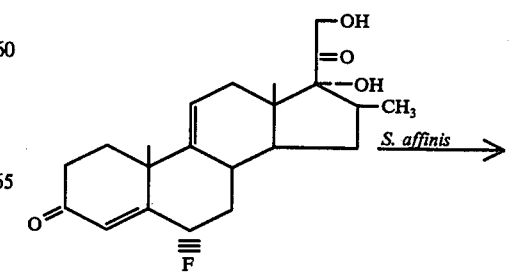

XXVI

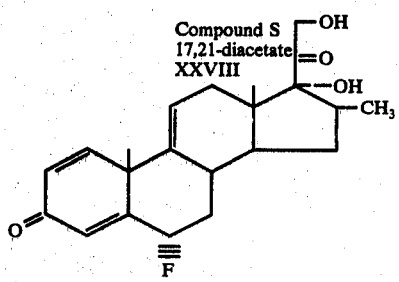

Compound S 17,21-diacetate XXVIII    XXVII

Evidence for the necessity of controlling both the pH so that it does not exceed 7.0 and having the C-17 tertiary alcohol esterified is demonstrated by the results of the Experiments (7-14) which are tabulated in Table 2.

TABLE 2

| SUBSTRATE | Experiment | PRODUCTS No Buffer | Experiment | Buffer pH = 6.2 |
|---|---|---|---|---|
| Compound S XIX | 7 | Androsta-1,4-diene-3,17-dione XVI  17β-hydroxy-androsta-1,4-diene-3-one XVII  Δ¹-testololactone XVIII | 11 | Androsta-1,4-diene-3,17-dione XVI  17β-hydroxyandrosta-1,4-diene-3-one XVII  Δ¹-testololactone XVIII |
| Compound S 21-acetate XXX | 8 | Androsta-1,4-diene-3,17-dione XVI  17β-hydroxyandrosta-1,4-diene-3-one XVII  Δ¹-testololactone XVIII | 12 | Androsta-1,4-diene-3,17-dione XVI  17β-hydroxyandrosta-1,4-diene-3-one XVII  Δ¹-testololactone XVIII |
| Compound S 17-acetate XXXI | 9 | Androsta-1,4-diene-3,17-dione XVI  17β-hydroxyandrosta-1,4-diene-3-one XVII  Δ¹-testololactone XVIII | 13 | Δ¹-Compound S-17-acetate XXIX |
|  | 10 | Androsta-1,4-diene-3,17-dione XVI  17β-hydroxyandrost-1,4-diene-3-one XVII  Δ¹-testololactone XVIII | 14 | Δ¹-Compound S-17-acetate XXIX |

However, the above reaction proceeds very slowly and is only about 20% complete after six days which is not useful commercially. See Example 5.

Evidence of the critical requirement of regulating the pH so that it does not exceed 7.0 is seen by looking at Table 1.

TABLE I

Bioconversion of Compound S-17,21-diacetate XXVIII by S. affinis with or without pH Control

| Substrate Level g./l. | Incubation time* | pH Control | Major Compound Formed | Chemical Yield | Experiment |
|---|---|---|---|---|---|
| 0.5 | 24 hours | 6.0 ± 0.5 | Δ¹-Cpd S-17-acetate XXIX | 28.9 | 6a |
| 1.0 | 48 hours | 6.0 ± 0.5 | Δ¹-Cpd S-17-acetate XXIX | 45.6 | 6b |
| 1.0 | 48 hours | No control** | Δ¹-testololactone XVIII | 19.7 | 6c |

*Time of incubation after substrate addition.
**pH was 7.0 or greater during steroid bioconversion phase.

The experimental data on which Table 1 is based is found in Examples 6a, 6b, and 6c. The results show that when Compound S-17,21-diacetate XXVIII is fermented with S. affinis and the pH is controlled so that it does not exceed 7.0 the major product is Δ¹-Compound S-17-acetate XXIX. When the pH is 7.0 or greater during the Δ¹ dehydrogenation the C-17 side chain is degraded and the major product is Δ¹-testololactone XVIII.

The results in Table 2 demonstrate that in all cases where the pH is not controlled the C-17 side chain is degraded to the 17-keto compound XVI, the 17β-hydroxy compound XVII and the 6 member D ring lactone XVIII. This degradation of the C-17 side chain even took place in both cases where the C-17 tertiary alcohol was esterified. The results of Table 2 further show that when the pH of the fermentation medium is controlled, here at pH = 6.2, and the C-17 tertiary alcohol is esterified the C-17 side chain is not degraded. However, even with the pH controlled the C-17 side chain is degraded unless it is esterified. These results show the necessity for requiring (1) C-17 esterification and (2) controlling the pH so that it does not exceed 7.0.

Chart B shows the results of the Δ¹ dehydrogenation of four different corticoid 17-esters with S. affinis under

CHART B

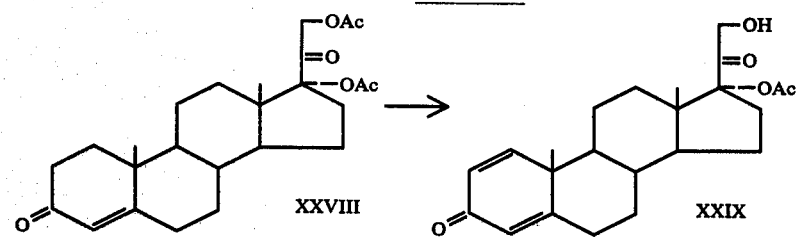

CHART B

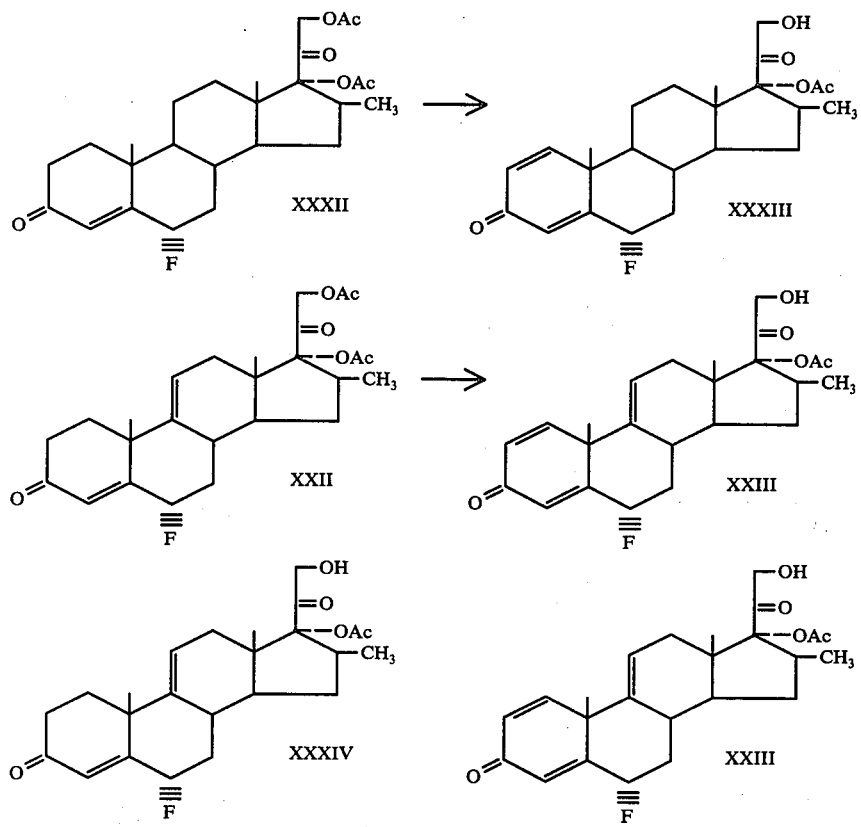

conditions in which the pH did not exceed 7.0. In all cases there is no degradation of the side chain.

Compound S-17,21-diacetate (17α,21-dihydroxypregna-4-ene-3,20-dione-17,21-diacetate) XXVIII, fermented with S. affinis at a pH of 6.2 yields the product Δ¹-Compound S-17-acetate (17α,21-dihydroxypregna-1,4-diene-3,20-dione-17-acetate) XXIX. See Example 14. Examples 6a and 6b ferment the same substrate with S. affinis producing the same product at a pH of 6.0 ± 0.5.

6α-Fuoro-16β-methyl-17α,21-dihydroxypregna-4-ene-3,20-dione-17,21-diacetate XXXII is fermented with S. affinis at a pH of 6.0 ± 0.5 and yields the product 6α-fluoro-16β-methyl-17α,21-dihydroxypregna-1,4-diene-3,20-dione-17-acetate XXXIII in one day. See Example 15.

6α-Fluoro-16β-methyl-17α,21-dihydroxypregna-4,9(11)-diene-3,20-dione-17,21-diacetate XXII is fermented with S. affinis at a pH of 6.0 and yields 6α-fluoro-16β-methyl-17α,21-dihydroxypregna-1,4,9(11)-triene-3,20-dione-17-acetate XXIII in two days. See Example 1. See also Examples 2 and 3.

A mono-ester, 6α-fluoro-16β-methyl-17α,21-dihydroxypregna-4,9(11)-diene-3,20-dione-17-acetate XXXIV is fermented with S. affinis at a pH less than 7.0. The product produced is 6α-fluoro-16β-methyl-17α,21-dihydroxypregna-1,4,9(11)-triene-3,20-dione-17-acetate XXIII. See Example 16.

Chart B demonstrates that if a corticoid 17-ester within the scope of compound XXI is fermented with a fungus of the genus Septomyxa under conditions where the pH is controlled and is not permitted to exceed 7.0 no degradation of the resulting Δ¹-steroid XX occurs.

Hydrolysis of the C-21 ester if present is not considered degradation since the C-21 primary alcohol can readily be re-esterified if desired by methods well known to those skilled in the art.

The improved process of the present invention is the Δ¹ dehydrogenation of corticoid substrates by Septomyxa with prevention of C-17 side chain degradation by controlling the pH so that it does not exceed 7.0 during the biotransformation. The corticoid substrate has the formula:

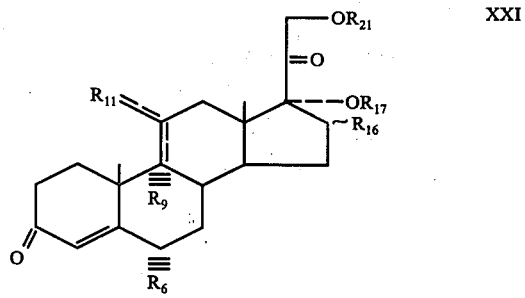

where $R_6$, $R_9$, $R_{11}$, $R_{16}$, $R_{17}$, $R_{21}$, $\sim$, and --- are all defined previously.

The substrate selected for Δ¹ dehydrogenation is added to the medium in any suitable form, either as a dry powder, a solution or an aqueous suspension. Non-toxic solvents, such as DMF, THF, and the like are well known to those skilled in the art. The bioconversion of the present invention is performed at substrate concentrations as high as 20 g./liter of fermentation medium. The preferred range of substrate concentrations is from about 0.5 to about 5 g./liter.

The temperature during the biotransformation is the same as that found suitable for growth of the microorganism. It need be maintained only within such a range as supports life, active growth or the enzyme activity of the microorganism. A range of 20° to 35° is preferred.

Aeration can be effected by surface culture in shake flasks or preferably by use of submerged fermentation conditions with air sparging, in accordance with methods well known in the art.

The time required for the bioconversion can vary considerably and is not critical. The range of about 2 to 100 hours is practical but not limiting; about 24 to 72 hours is generally satisfactory.

After completion of the fermentation, the resulting $\Delta^1$ dehydrogenated product XX is recovered from the fermentation medium by conventional methods. The fermentation medium can be extracted with a water-immiscible organic solvent such as methylene chloride, chloroform, carbon tetrachloride, ethylene chloride, trichlororethylene, diethyl ether, butyl acetate, amyl acetate, benzene, methyl-isobutyl-ketone and the like or the fermentation medium and mycelia can be separated by conventional methods such as centrifugation or filtration, and then separately extracted with suitable solvents. The mycelia can be extracted with either water-miscible or water immiscible solvents or in cases where little or no product is contained in the mycelium, it can be merely washed with water and the wash water added to the filtrate. The filtrate, free of mycelia, can then be extracted with water-immiscible solvents such as those listed above. The extracts are combined, dried over a drying agent such as anhydrous sodium sulfate, and the solvent removed to concentrate the mixture by conventional methods such as evaporation or distillation at atmospheric or reduced pressure.

The compounds obtained by the claimed process, can be further purified by conventional methods such as chromatography or recrystallization from suitable organic solvents.

The invention may be more fully understood from the following examples.

All temperatures are in degrees centigrade.
TLC refers to thin-layer chromatography.
THF refers to tetrahydrofuran.
DMF refers to dimethylformamide.
DDQ refers to 2,3-dichloro-5,6-dicyano-1,4-benzoquinone.
SSB refers to Skellysolve B, an isomeric mixture of hexanes.
IR refers to infrared.
IR absorption spectra are recorded on a Perkin-Elmer model 421 spectrophotometer.
NMR refers to nuclear magnetic resonance.
NMR spectra are recorded on a Varian A-60 spectrophotometer with tetramethylsilane as an internal standard.
Mass spectra are recorded on an Atlas CH-4 mass spectrometer with a TO-4 source (ionization voltage 70 ev) or a CEC 110B High Resolution Mass Spectrometer.
Melting points are determined on a Fisher-Johns melting point apparatus.
UV refers to ultraviolet.
Ac refers to acetyl (-COCH$_3$).

Preparation 1

Compound S-17-acetate XXXI (Formula XXI: $R_6$, $R_9$, $R_{16}$, and $R_{21}$ are hydrogen, $R_{11}$ is H,H, and $R_{17}$ is Ac)

Compound S-17-acetate XXXI is prepared from Compound S-17,21-diacetate (Steroids, Fieser and Fieser, Reinhold Publishing Co., New York, 1959, p. 679) by selective deacylation using *Flavobacterium dehydrogenans* at pH 6.2.

*F. dehydrogenans* is grown on the following fermentation medium:

| Item | g./l. |
| --- | --- |
| Yeast Extract (Difco) | 10.0 |
| Na$_2$HPO$_4$ | 4.5 |
| KH$_2$PO$_4$ | 3.4 |

The pH is adjusted to 6.2 with 5.0 N hydrochloric acid. Fermentation medium (100 ml.) is placed in 500 ml. Erlenmeyer flasks, autoclaved and inoculated.

Incubation is carried out at 28° on a 257 rpm rotary shaker.

Prior to substrate addition 25 ml. of 1.0 M potassium phosphate buffer, pH 6.2, is added to each flask and the pH of the medium adjusted to 6.2 with 5.0 N hydrochloric acid. Compound S-17,21-diacetate (0.2 g.) is added to each flask suspended in 1 ml. of water. Bioconversion is continued for 28 hours. The pH is maintained at 6.2 by the addition of 5.0 N hydrochloric acid. After 28 hours the contents of the flasks are pooled, and extracted with an equal volume of methyl-isobutyl-ketone. The extract is concentrated under reduced pressure to dryness.

The crude extract is chromatographed on silica gel (30 g.) in benzene. Elution is performed with increasing percentages of ethyl acetate. The residue obtained by concentration of selected fractions is recrystallized from aqueous methanol to give the title compound, m.p. 196°–206°; $[\alpha]_D$ +49° (chloroform); NMR (CDCl$_3$ - 1% TMS) 0.70, 1.20, 2.08, 4.30 and 5.78$\delta$; IR (mull) 3460, 1730, 1670 and 1612 cm$^{-1}$; UV (ethanol) $\lambda$max. = 240.5 nm ($\epsilon$ = 16,950); mass spectrum 388, 357, 328, 315, 131 m/e.

Preparation 2

6$\alpha$-Fluoro-16$\beta$-methyl-17$\alpha$,21-dihydroxypregna-4-ene-3,20-dione 17,21-diacetate XXXII (Formula XXI: $R_6$ is fluorine, $R_9$ is hydrogen, $R_{11}$ is H,H, $R_{16}$ is methyl, $R_{17}$ and $R_{21}$ are acetate and ∼ is beta)

The title compound is prepared from 6$\alpha$-fluoro-16$\beta$-methyl-17$\alpha$,21-dihydroxypregna-4-ene-3,20-dione (U.S. Pat. No. 3,174,865, formula XI) by methods well known to those skilled in the art such as acetic anhydride in pyridine.

Preparation 3

6$\alpha$-fluoro-16$\beta$-methyl-17$\alpha$,21-dihydroxypregna-4,9(11)-diene-3,20-dione XXVI 6$\alpha$-Fluoro-16$\beta$-methyl-17$\alpha$,21-dihydroxypregna-4,9(11)-diene-3,20-dione 21-acetate (U.S. Pat. No. 3,557,158, Example 15A) is dissolved in methanol, added to a mixture of potassium carbonate in methanol and stirred. When the hydrolysis of the 21-acetate is complete as measured by TLC the title compound is isolated by means well known to those skilled in the art.

Preparation 4

6α-fluoro-16β-methyl-17α,21-dihydroxypregna-4,9(11)-diene-3,20-dione 17-acetate XXXIV (Formula XXI: $R_6$ is fluorine, $R_9$ is not present, $R_{11}$ is H, $R_{16}$ is methyl, $R_{17}$ is acetate, $R_{21}$ is hydrogen $\sim$ is beta, $=\!=\!=$ in the C ring is a double bond and$=\!=\!=$between $R_{11}$ and $C_{11}$ is a single bond)

6α-Fluoro-16β-methyl-17α,21-dihydroxypregna-4,9(11)-diene-3,20-dione (5.0 g., Preparation 3) is suspended in 100 ml. of benzene. The solution is heated to boiling and a small amount of benzene distilled off. p-Toluene sulfonic acid (25 mg.) is added followed by the addition of trimethylorthoacetate (2.5 ml.). The reaction mixture is allowed to distill slowly. After 15 minutes additional p-toluene sulfonic acid (15 mg.) is added and heated for another 5 minutes. TLC (chloroform-methanol, 19-1) showed an absence of starting material. The mixture is cooled and 2 ml. of 2% of triethylamine in benzene is added. The solution is washed with 1 N potassium bicarbonate, dried over sodium sulfate and condensed to a foam which is crystallized from acetone-SSB (containing pyridine) to give yellow sticky crystals. The crystals are boiled briefly with methanol (10 ml.), the mixture cooled and filtered to give 6α-fluoro-16β-methyl-17α,21-dihydroxypregna-4,9(11)-diene-3,20-dione 17,21-methylorthoacetate. NMR ($CDCl_3$ - 1% TMS) 0.68, 1.17, 1.34, 1.55, 3.22, 3.87, 4.02, 4.71–5.1, 5.5–5.9, and 6.07δ.

The orthoacetate is boiled with methanol (230 ml.) and cooled to 25° under nitrogen. A potassium acid phthalate solution, pH 3.0 (50 ml., 0.05 M) is added and accompanied by deposition of a heavy white precipitate. The mixture is stirred at about 25° for 24 hours. The mixture is concentrated under reduced pressure (bath $\leqq$ 30°) to a thick slurry. The thick slurry is diluted to 500 ml. with water and stirred for 1 hour. The product is isolated and dried under vacuum at 80° to yield 3.59 gm. The product is crystallized from acetate-SSB to give the title compound, m.p. 194°–196°; IR (mull) 3420, 1730, 1655, 1610, 1235, 1095, 1070, 1025, 965, 880 cm$^{-1}$.

EXAMPLE 1

6α-fluoro-16β-methyl-17α,21-dihydroxypregna-1,4,9(11)-triene-3,20 dione 17-acetate XXIII (Formula XX: $R_6$ is fluorine, $R_9$ is not present, $R_{11}$ is H, $R_{16}$ is methyl, $R_{17}$ is acetate, is beta,$=\!=\!=$in the C ring is a double bond and$=\!=\!=$between $R_{11}$ and $C_{11}$ is a single bond)

Refer to Chart A a. Seed medium SD-10

| Ingredient | Concentration (g./l.) |
| --- | --- |
| Cornsteep liquor | 20 |
| Glucose | 10 |
| Distilled water | q.s.a.d. |

The seed medium is mixed, 100 ml. placed in 500 ml. Erlenmeyer flasks and sterilized as is known in the art. The shake flasks are inoculated with *S. affinis*, ATCC 6737, from slants as is known in the art and placed on a shaker for 72 hours at 28°.

b. Fermentation medium SD-10

| Ingredient | Concentration (g./l.) |
| --- | --- |
| Cornsteep liquor | 20 |
| Glucose | 10 |
| Distilled Water | q.s.a.d. |

The fermentation medium is mixed, 100 ml. placed in 500 ml. Erlenmeyer flasks and sterilized as is well known in the art. The shake flasks are inoculated with 2.0 ml. or 5.0 ml. of the seed culture as is known in the art and placed on a shaker for 24 hours at 28°.

c. Inducer

Bisnoraldehyde is added to give a final concentration of 0.05 g./l. about 3 hours prior to substrate addition.

d. pH Control - buffering

Just prior to substrate addition 10 ml. of 1.0 M potassium phosphate buffer pH 6.0 is added to each shake flask so that the final buffer concentration in the fermentation medium is approximately 0.1 M.

e. Substrate Addition

6α-Fluoro-16β-methyl-17α,21-dihydroxypregna-4,9(11)-diene-3,20-dione 17,21-diacetate (German Offen. 2,308,731, Example 1) is dissolved in DMF (50 mg./ml.) and 1 ml. is added to each shake flask to give a substrate concentration of 0.5 g./l.

f. Fermentation (bioconversion)

The fermentation is carried out for 48 hours at 28° on the rotary shaker.

g. Extraction

The fermentation medium is extracted 3 times with equal volumes of methylene chloride. The methylene chloride extract is concentrated to dryness.

h. Isolation and Purification

The crude extract from the bioconversion of the substrate is purified by TLC in chloroform-ethyl acetate (2-1).

The main zone is the title compound, m.p. 225°–226°; UV (95% ethanol) λmax. = 236 nm (ε = 16,700); IR (mull) 3460, 1730, 1710, 1670, 1630, 1610 sh., 1275, 1250, 1090, 1065, 1035, 990 and 900 cm$^{-1}$; NMR ($CDCl_3$ - 1% TMS) 0.68, 1.41, 1.42, 2.10, 4.08, and 5.4δ.

EXAMPLE 2

6α-fluoro-16β-methyl-17α,21-dihydroxypregna-1,4,9(11)-triene-3,20-dione 17-acetate XXIII (Formula XX: $R_6$ is fluorine, $R_9$ is not present, $R_{11}$ is H, $R_{16}$ is methyl, $R_{17}$ is acetate, $\sim$ is beta, $=\!=\!=$in the C ring is a double bond and $=\!=\!=$between $R_{11}$ and $C_{11}$ is a single bond)

Refer to Chart A

Following the general procedure of Example 1 but making non-critical variations in the volume of fermentation medium (3 l. in a 5 l. fermentor), substrate concentration (1.0 g./liter) and length of fermentation (111 hours) 6α-fluoro-16β-methyl-17α,21-dihydroxypregna-4,9(11)-diene-3,20-dione-17,21-diacetate (German Offen. 2,308,731, Example 1) is used as a substrate. Following the bioconversion the fermentation medium is extracted and purified. The fermentation filtrate is extracted twice with one-sixth the fermentation volume of methylene chloride. The cake is extracted three times with one-sixth the fermentation volume of methanol. Each extraction with methanol requires 30 minutes stirring at room temperature. The methylene chloride extracts are evaporated, the residue combined with the methanol extracts of the fermentation cake and the mixture is concentrated to one-sixth the volume of the fermentation medium. This concentrate (approximately 75% aqueous methanol) is defatted by extracting 3 times with one-eighth the concentrate volume of methylene chloride-SSB (1-4). The fat extracts are combined and backwashed with one-third the volume of 20% aqueous methanol. The defatted concentrate and backwash are combined, concentrated and refrigerated overnight yielding crystals. The crystals are filtered, washed with water and SSB and dried at 50° under vacuum. The resulting crystals are the title compound obtained in 89% yield. $R_f = 0.44$ (10% acetone in chloroform).

EXAMPLE 3

6α-fluoro-16β-methyl-17α,21-dihydroxypregna-1,4,9(11)-triene-3,20-dione 17-acetate XXIII (Formula XX: $R_6$ is fluorine, $R_9$ is not present $R_{11}$ is H, $R_{16}$ is methyl, $R_{17}$ is acetate, ⁓ is beta, ⁼⁼⁼ in the C ring is a double bond and ⁼⁼⁼ between $R_{11}$ and $C_{11}$ is a single bond)

Refer to Chart A

Following the exact procedure of Example 2, but fermenting for 113 hours the title compound is isolated in 88% yield. $R_f = 0.44$ (10% acetone in chloroform).

EXAMPLE 4

6α-fluoro-16β-methyl-17α,21-dihydroxypregna-1,4,9(11)-triene-3,20-dione 17-acetate XXIII (Formula XX: $R_6$ is fluorine, $R_9$ is not present, $R_{11}$ is H, $R_{16}$ is methyl, $R_{17}$ is acetate, ⁓ is beta, ⁼⁼⁼ in the C ring is a double bond and ⁼⁼⁼ between $R_{11}$ and $C_{11}$ is a single bond)

Refer to Chart A

Following the procedure of Example 1 but replacing the phosphate buffer with an automatic pH control system as is well known in the art which adds a sufficient amount of 0.05 M hydrochloric acid to the fermentation medium when necessary to maintain the pH at 7.0, the title compound is produced.

EXAMPLE 5

6α-fluoro-16β-methyl-17α,21-dihydroxypregna-1,4,9(11)-triene-3,20-dione XXVII

Following the procedure of Example 1 but not controlling the pH of the fermentation 6α-fluoro-16β-methyl-17α,21-dihydroxypregna-4,9(11)-diene-3,20-dione XXVI (Preparation 3) is used as the substrate. The bioconversion takes place very slowly and is only about 20% complete after 6 days yielding the title compound.

EXAMPLE 6

Comparison of Fermenting Compound S-17,21-diacetate XXVIII with and without pH Control (a) With pH Control (pH = 6.0, 0.5 g./l. substrate)

Following the general procedure of Example 1 but making non-critical variations in volume of fermentation medium (3 l. in a 5 l. fermentor), fermentation time (24 hours), Compound S-17,21-diacetate XXVIII (Steroids, Fieser and Fieser, Reinhold Publishing Co., New York, 1959, p. 679) is used as the substrate (0.5 g./l.).

Following extraction the crude extract is partitioned between methanol-water (4-1) and hexane-chloroform (9-1). The lower phase contained 5.05 g. of a yellow oil. The oil is partitioned between methanol-water (80-20) and methylene chloride-SSB (20-80). The oil from the methanol-water phase (3.07 g.) is chromatographed on a silica gel column which is eluted with ethyl acetate-chloroform (1-3). The fractions containing steroid are pooled, concentrated and crystallized from ethyl acetate-SSB to give Δ¹-Compound S 17-acetate XXIX (0.43 g., 28.9% yield), IR (KBr) 1740, 1685 and 1605 cm⁻¹; NMR (CDCl₃ - 1% TMS) 0.74, 1.16, 2.06, 4.30, 6.14, 6.34, 6.38, 7.0 and 7.18δ.

(b) With pH Control (pH = 6.0, 1.0 g./l. substrate)

The procedure above is followed except the substrate concentration is 1.0 g./l. Following extraction and concentration the crude extract is diluted with a large volume of SSB and left to stand overnight. The SSB is decanted leaving a semicrystalline material which is dissolved in chloroform and decolorized with activated carbon. The solvent is evaporated and the residue recrystallized from ethyl acetate-SSB to give colorless needles of Δ¹-Compound S 17-acetate XXIX (1.19 gm., 45.6% yield) m.p. 172.5–180.5°; $[\alpha]_D$ -9.4° (CHCl₃).

(c) Without pH Control (1.0 g./l.)

The procedure of Example 6(b) above is followed except the buffer is not added and the pH is permitted to follow its normal course. Following extraction and concentration the crude semi-solid extract is dissolved in ethyl acetate and decolorized by filtration through activated carbon, concentrated and cooled to give 415 mg. of colorless crystals. Recrystallization from ethyl acetate-hexane yields Δ¹-testololactone XVIII, IR (KBr) 1710, 1660, and 1620 cm⁻¹; NMR (CDCl₃ - 1% TMS) 1.21, 1.38, 6.10, 6.14, 6.16, 6.32, 6.34, 6.98, and 7.14δ; mass spectrum (m/e) 300 and 122.

EXAMPLE 7

Compound S XIX and no buffer

Following the general procedure of Example 1 but making non-critical variations of inducer (omitted), fermentation time (24 hours) Compound S XIX is used as the substrate. The pH is not controlled by buffer or any other means. After 24 hours of fermentation the fermentation medium is extracted 3 times with methylisobutyl-ketone. The extract is concentrated to dryness. The products androsta-1,4-diene-3,17-dione XVI, 17β-hydroxyandrosta-1,4-diene-3-one XVII and Δ¹-testololactone XVIII are identified by TLC in methylene chloride-methanol-water-acetic acid (90-7-1-2), $R_f$ = .70, .50 and .45, respectively.

EXAMPLE 8

Compound S-21-acetate XXX and no buffer

Following the procedure of Example 7 Compound S 21-acetate XXX (Merck Index, 8th Edition, Merck & Co., Rahway, N. J., 1968, p. 333) is used as the substrate. The pH is not controlled by buffer or any other means. The products androsta-1,4-diene-3,17-dione XVI, 17β-hydroxyandrosta-1,4-diene-3-one XVII and Δ¹-testololactone XVIII are identified by TLC in methylene chloride-methanol-water-acetic acid (90-7-1-2), $R_f$ = .70, .50, and .45, respectively.

EXAMPLE 9

Compound S-17-acetate XXXI and no buffer

Following the procedure of Example 7 Compound S 17-acetate XXXI (Preparation 1) is used as the substrate. The pH is not controlled by buffer or any other means. The products androsta-1,4-diene-3,17-dione XVI, 17β-hydroxyandrosta-1,4-diene-3-one XVII and Δ¹-testololactone XVIII are identified by TLC in methylene chloride-methanol-water-acetic acid (90-7-1-2), $R_f = .70, .50,$ and $.45$, respectively.

EXAMPLE 10

Compound S-17,21-diacetate XVIII and no buffer

Following the procedure of Example 7 Compound S-17,21-diacetate XXVIII (Steroids, Fieser and Fieser, Reinhold Publishing Co., New York, 1959, p. 679) is used as the substrate. The pH is not controlled by buffer or any other means. The products androsta-1,4-diene-3,17-dione XVI, 17β-hydroxyandrosta-1,4-diene-3-one XVII and Δ$^1$-testololactone XVIII are identified by TLC in methylene chloride-methanol-water-acetic acid (90-7-1-2), $R_f = .70, .50$ and $.45$, respectively.

EXAMPLE 11

Compound S XIX and Buffer pH = 6.2

Following the general procedure of Example 1 but making non-critical variations of inducer (omitted), fermentation time (24 hours) Compound S XIX is used as the substrate. The pH of the fermentation medium is controlled by a 0.1 M phosphate buffer of pH 6.2. After 24 hours of fermentation the fermentation medium is extracted 3 times with methyl-isobutyl-ketone. The extract is concentrated to dryness. The products androsta-1,4-diene-3,17-dione XVI, 17β-hydroxyandrosta-1,4-diene-3-one XVII and Δ$^1$-testololactone XVIII are identified by TLC in methylene chloride-methanol-water-acetic acid (90-7-1-2), $R_f = .70, .50,$ and $.45$, respectively.

EXAMPLE 12

Compound S-21-acetate XXX and Buffer pH = 6.2

Following the procedure of Example 11 Compound S-21-acetate is used as the substrate. The pH of the fermentation medium is controlled by a 0.1 M phosphate buffer pH 6.2. The products androsta-1,4-diene-3,17-dione XVI, 17β-hydroxyandrosta-1,4-diene-3-one XVII and Δ$^1$-testololactone XVIII are identified by TLC in methylene chloride-methanol-water-acetic acid (90-7-1-2), $R_f = .70, .50,$ and $.45$, respectively.

EXAMPLE 13

Compound S-17-acetate XXXI and Buffer pH = 6.2

Following the procedure of Example 11 Compound S-17-acetate is used as the substrate. The pH of the fermentation medium is controlled by a 0.1 M phosphate buffer pH 6.2. The product of the fermentation, Δ$^1$-Compound S-17-acetate XXIX, is identified by TLC in methylene chloride-methanol-water-acetic acid (90-7-1-2). The $R_f$ is 0.60.

EXAMPLE 14

Compound S-17,21-diacetate and Buffer pH = 6.2

Following the procedure of Example 11 Compound S-17,21-diacetate is used as the substrate. The pH of the fermentation medium is controlled by a 0.1 M phosphate buffer pH 6.2. The crude extract from the bioconversion is purified by TLC on 3 plates (20 cm. × 40 cm.) in chloroform-ethyl acetate (2-1). The main zone is a colorless oil that crystallizes in contact with ethyl acetate. Recrystallization from ethyl acetate gives Δ$^1$-Compound S-17-acetate XXIX, m.p. 192°–193°; UV (95% ethanol), λmax. = 243 nm (ε = 16,150); IR (mull) 3410, 1730, 1655, 1615, 1600, and 1230 cm$^{-1}$; NMR (CDCl$_3$ - 1% TMS) 0.74, 1.26, 2.05, 4.26, 6.12, 6.16, 6.34, 7.0, and 7.16 ppm; [α]$_D$ -15° (chloroform).

EXAMPLE 15

6α-fluoro-16β-methyl-17α,21-dihydroxypregna-1,4-diene-3,20-dione 17-acetate XXXIII (Formula XX: R$_6$ is fluorine, R$_9$ is hydrogen, R$_{11}$ is H,H, R$_{16}$ is methyl, R$_{17}$ is acetate and ⌣ is beta)

Refer to Chart B

Following the general procedure of Example 1, 6α-fluoro-16β-methyl-17α,21-dihydroxypregna-4-ene-3,17-dione 17,21-diacetate XXXII is used as the substrate (2.8 g., Preparation 2). The pH is maintained at 6.0 ± 0.5 and the bioconversion is complete in 24 hours yielding the title compound, m.p. 229°–233.5°; UV (95% ethanol), λmax. = 242 nm (ε = 17,500); IR (mull) 3430, 1730, 1655, 1615, 1595, 1235, 1225, 1195, 1065, 1020, 970, 935, 890, and 820 cm$^{-1}$; NMR (CDCl$_3$ - 1% TMS) 0.76, 1.23, 1.39, 2.10, 4.08, 5.25, 6.14–6.50, 6.85–7.20δ.

EXAMPLE 16

6α-fluoro-16β-methyl-17α,21-dihydroxypregna-1,4,9(11)-triene-3,20-dione 17-acetate XXIII (Formula XX: R$_6$ is fluorine, R$_9$ is not present, R$_{11}$ is H, R$_{16}$ is methyl, R$_{17}$ is acetate, ⌣ is beta,⩭in the C ring is a double bond, and⩭between R$_{11}$ and C$_{11}$ is a single bond)

Refer to Charts A and B

Following the general procedure of Example 1 but making non-critical variations in fermentation time (78 hours) and number of shake flasks (3) 6α-fluoro-16β-methyl-17α,21-dihydroxypregna-4,9(11)-diene-3,20-dione 17-acetate XXXVI (Preparation 4) is used as the substrate. After 78 hours of fermentation the contents of the flasks are pooled and extracted 3 times with methylene chloride. The title compound is identified by TLC methylene chloride-methanol-water-acetic acid (90-7-1-2), $R_f = .60$.

EXAMPLE 17

Biotransformation with Washed Cells

Septomyxa is grown on a seed medium and fermentation medium according to Example 1. After 24 hours of growth at 28° the mycelium is harvested from the fermentation medium. The mycelia are suspended in 0.1 molar potassium phosphate buffer pH 6.0. Compound S 17,21-diacetate XXVIII is dissolved in DMF (50 mg./ml.) and a sufficient amount is added to each flask to give a final substrate concentration of 0.5 g./l. The substrate is stirred with the mycelium for 48 hours at 28°. The biotransformation medium is filtered to remove the mycelium and the filtrate is extracted 3 times with methylene chloride. The crude extract from the bioconversion of the substrate is purified by TLC in chloroform-ethyl acetate (2-1). The product is Δ$^1$-Compound S 17-acetate XXIX.

EXAMPLE 18

Biotransformation with Dried Cells

Septomyxa is grown and harvested according to the general outline procedure of Example 1. The mycelium is dried as is well known in the art. The dried mycelia are suspended in 0.1 molar potassium phosphate buffer pH 6.0. Substrate addition, biotransformation, isolation and purification are performed according to Example 17. The product is Δ¹-Compound S 17-acetate XXIX.

EXAMPLE 19

Biotransformation for the Enzyme Preparation from Septomyxa Preinduced so as to contain the Δ¹-Dehydrogenase Septomyxa is grown and the Δ¹-dehydrogenase is induced according to the general outline procedure of Example 1. The mycelium is harvested and the Δ¹-dehydrogenase is obtained from the mycelium by methods well known to those skilled in the art. The enzyme preparation is diluted with 0.1 molar potassium phosphate buffer, pH 6.0 to give an enzyme potency of 2000 DU/ml. [H. J. Koepsell, Biotech & Bioeng 4, 65 (1962)]. The enzyme is added to the substrate to give a final steroid concentration of 0.5 g./l. and the biotransformation, extraction, isolation and purification are performed as according to the procedure set forth in Example 17. The product is Δ¹-Compound S 17-acetate XXIX.

I claim:

1. An improved biotransformation process for the production of a steroid of the formula:

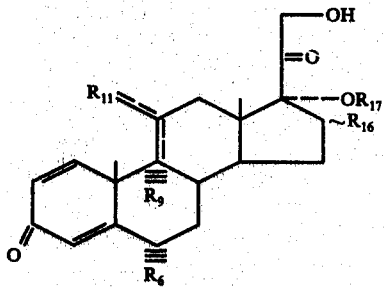

XX where $R_6$ is a hydrogen or fluorine atom or methyl group; where $R_9$ when present is a hydrogen, fluorine, chlorine, or bromine atom, or hydroxyl group; where $R_{11}$ is (H), (H,H) (H,αOH), (H,βOH), or (O); where $R_{16}$ is a hydrogen atom or methyl group; where $R_{17}$ is alkyl carboxylate of 2 thru 6 carbon atoms, aromatic carboxylate of 7 thru 12 carbon atoms, where ~ indicates the attachment of the $R_{16}$ group in the alpha or beta configuration; and where≡≡≡is a single or double bond where a compound of the formula:

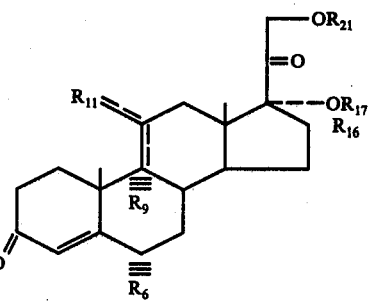

XXI where $R_6$, $R_9$, $R_{11}$, $R_{16}$, $R_{17}$, ~ and≡≡≡are defined above and where $R_{21}$ is a hydrogen atom, alkyl carboxylate of 2 thru 6 carbon atoms is contacted aerobically in a fermentation medium with a fungus of the genus Septomyxa followed by extraction and purification the improvement comprises controlling the pH of the medium so that the pH is controlled and does not exceed 7.0.

2. A process according to claim 1 where the method of contacting is by fermentation with a vegetative growth.

3. A process according to claim 2 where the fungus is *S. affinis*.

4. A process according to claim 3 where the pH is controlled by a physiological buffer.

5. A process according to claim 4 where the pH does not exceed 6.8.

6. A process according to claim 5 where the pH does not exceed 6.5.

7. A process according to claim 6 where the steroid XX is difluorasone-17-acetate.

8. A process according to claim 6 where the steroid XX is 6α-fluoro-16β-methyl-17α,21-dihydroxypregna-1,4,9(11)-triene-3,20-dione-17-acetate.

9. A process according to claim 3 where the pH is controlled automatically.

10. A process according to claim 9 where the pH does not exceed 6.8.

11. A process according to claim 10 where the pH does not exceed 6.5.

12. A process according to claim 11 where the steroid XX is difluorasone-17-acetate.

13. A process according to claim 11 where the steroid XX is 6α-fluoro-16β-methyl-17α,21-dihydroxypregna-1,4,9(11)-triene-3,20-dione-17-acetate.

14. An improved fermentative process for the production of 6α-fluoro-16β-methyl-17α,21-dihydroxypregna-1,4,9(11)-triene-3,20-dione-17-acetate where 6α-fluoro-16β-methyl-17α,21-dihydroxypregna-4,9(11)-diene-3,20-dione-17,21-diacetate is fermented aerobically in a fermentation medium with a vegetative growth of *Septomyxa affinis* followed by extraction and purification where the improvement comprises controlling the pH of the fermentation medium so that the pH is controlled and does not exceed 6.5.

* * * * *